US00PP32058P2

(12) United States Plant Patent
Fielding

(10) Patent No.: US PP32,058 P2
(45) Date of Patent: Aug. 11, 2020

(54) ***RANUNCULUS* PLANT NAMED 'ROCORANGE'**

(50) Latin Name: ***Ranunculus cortusifolius* x *asiaticus***
Varietal Denomination: ROCORANGE

(71) Applicant: John Fielding, London (GB)

(72) Inventor: John Fielding, London (GB)

( * ) Notice: Subject to any disclaimer, the term of this patent is extended or adjusted under 35 U.S.C. 154(b) by 0 days.

(21) Appl. No.: 16/501,917

(22) Filed: Jul. 2, 2019

(51) Int. Cl.
*A01H 5/02* (2018.01)
*A01H 6/72* (2018.01)

(52) U.S. Cl.
USPC ..... Plt./263.1
CPC ..... *A01H 6/72* (2018.05)

(58) Field of Classification Search
USPC ..... Plt./263.1
CPC ..... A01H 5/02
See application file for complete search history.

(56) References Cited

PUBLICATIONS https://thechattygardener.com/?p=9559; May 9, 2019; 5 pages.*
PLUTO Plant Variety Database Citation for 'Rocorange' as per QZ PBR 20181378; Aug. 16, 2018; 1 page.*

* cited by examiner

*Primary Examiner* — Kent L Bell
(74) *Attorney, Agent, or Firm* — Cassandra Bright

(57) ABSTRACT

A new and distinct *Ranunculus* cultivar named 'ROCORANGE' is disclosed, characterized by cold-hardy plants producing multiple bright orange, semi-double flowers per stem. The new variety is a *Ranunculus*, useful as an ornamental plant or for cut flower production.

2 Drawing Sheets

Figure 1:
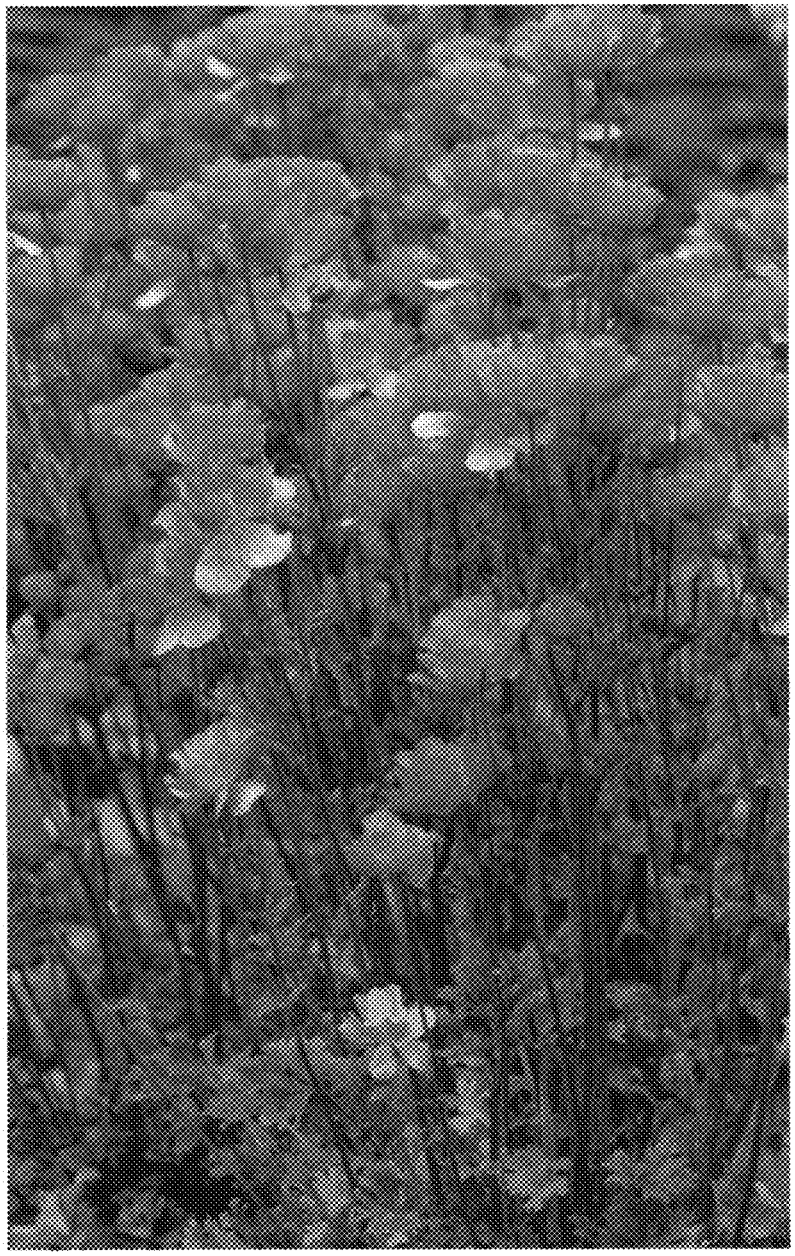

Latin name of the genus and species: *Ranunculus cortusifolius* x *asiaticus*.

Variety denomination: 'ROCORANGE'.

BACKGROUND OF THE INVENTION

The new *Ranunculus* cultivar is a product of a planned breeding program conducted by the inventor, John Fielding in London, United Kingdom at his home garden. The objective was to produce varieties that are garden hardy in zone 8, and suitable for cut flower or garden uses. The cross resulting in this new variety was made in April of 2004.

The seed parent is an unnamed, unpatented variety of *Ranunculus cortusifolius*. The pollen parent is an unnamed, unpatented variety of *Ranunculus asiaticus*. The new variety was discovered in April 2009 by the inventor in a group of seedlings resulting from the 2004 crossing, in London, United Kingdom.

Asexual reproduction of the new cultivar was first performed by division of tubers in July 2009 at the inventor's home garden. The unique features of this cultivar are stable and reproduced true to type in more than 10 successive generations. Date of first sale of the new cultivar was Oct. 1, 2018, in the Netherlands.

SUMMARY OF THE INVENTION

The cultivar 'ROCORANGE' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ROCORANGE' These characteristics in combination distinguish 'ROCORANGE' as a new and distinct *Ranunculus* cultivar:

1. Garden hardy in USDA Zone 7 or 8, observed to survive −15° Celsius in garden trials.
2. Can be used for cut flower or garden uses.
3. Cut flower will last in water for 12 to 14 days, with all flowers opening.
4. Branched stems with multiple flowers per stem.
5. Bright orange flower color.

PARENT COMPARISON

Plants of the new cultivar 'ROCORANGE' are similar to plants of the seed parent, in most horticultural characteristics, however, plants of the new cultivar 'ROCORANGE' differ in the following:

1. The seed parent is taller than the new variety.
2. Flowers of the new variety are bright orange, while the seed parent's flowers are golden yellow.
3. The seed parent has 5 petals per flower, while the new variety has typically more than 50 petals.

Plants of the new cultivar 'ROCORANGE' are similar to plants of the pollen parent, in most horticultural characteristics, however, plants of the new cultivar 'ROCORANGE' differ in the following:

1. The pollen parent is shorter than the new variety.
2. The pollen parent is less winter hardy than the new variety.
3. The pollen parent has fewer flowers per stem than the new variety.

COMMERCIAL COMPARISON

Plants of the new cultivar 'ROCORANGE' are comparable to the unpatented commercial variety *Ranunculus*

'Elegance Orange'. The two *Ranunculus* varieties are similar in most horticultural characteristics; however, the new variety 'ROCORANGE' differs in the following:

1. Vegetative carriage, foliage occurs lower on plants of the new variety.
2. Flower color of the new variety is a darker orange.
3. Vase life of flowers of the new variety is longer than that of this comparator.
4. The new variety is tolerant of more cold temperatures than this comparator.

BRIEF DESCRIPTION OF THE PHOTOGRAPHS

The accompanying photograph in FIG. 1 illustrates in full color flowering plants of the new variety at approximately 1 year old, grown outdoors.

Figure 2:
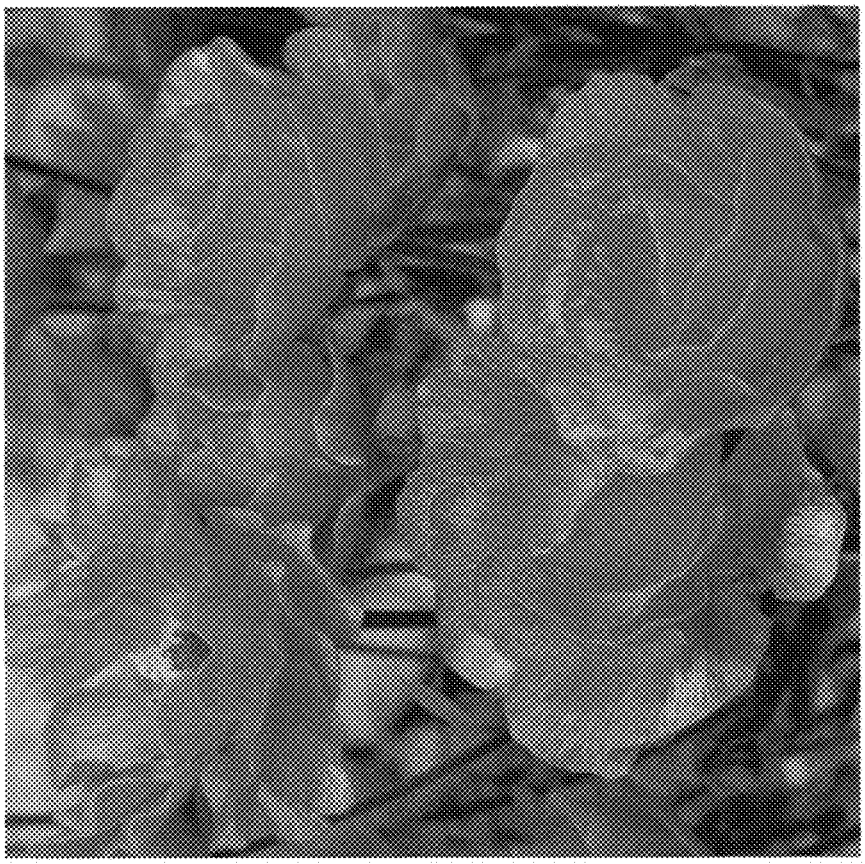

FIG. 2 illustrates a close-up view of flowers.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart $6^{th}$ edition, except where general terms of ordinary dictionary significance are used. The following observations and measurements describe 18-month-old 'ROCORANGE' plants grown in a vented, unheated polytunnel in London, United Kingdom. No chemical treatments were performed. The growing temperature ranged from 5° C. to 25° C. during the day and from −5° C. to 10° C. during the night. General light conditions are bright, normal sunlight. Measurements and numerical values represent averages of typical plant types. Botanical classification: *Ranunculus cortusifolius* x *asiaticus* 'ROCORANGE'.

PROPAGATION

Typical method: Tissue culture.
Time to rooting: 15 days at approximately 10-15° C.
Time to produce a rooted plantlet: 20 days.

PLANT

Root description: Secondary roots grow from the tuber and are fasciculate.
Growth habit: Herbaceous perennial, robust, semi-erect.
Height to top flower: Average 65 cm.
Plant spread: Average 40 cm.
Growth rate: Medium to strong.
Branching characteristics: Branched panicle.
Length of lateral branches: Average range 14 to 25 cm.
Diameter of lateral branches: Average range 0.3 to 0.5 cm.
Texture of lateral branches: Glossy, slightly tomentose.
Internode length: Very close, forming basal rosette.
Strength of lateral branches: Medium.
Color of lateral branches: Near RHS Yellow-Green 146A.
Aspect/angle of branches: 30° from vertical.
Number of leaves per lateral branch: Usually 2.

FOLIAGE

Basal leaf:

*Arrangement.*—Young Leaf: Trifoliate. Mature Leaf: Biternate.
*Average length.*—18 to 30 cm.
*Average width.*—12 to 15 cm.
*Overall shape of blade.*—Young Leaf: Obovate. Mature Leaf: Palmatifid to palmatipartite.
*Dissected leaves, describe lobes, quantity of dissection.*—Leaves generally lobed, in 3 parts, each further divided in 3 or more lobes. Lobes become more pronounced as leaf ages.
*Apex.*—Young leaf: Rounded. Mature leaf: Acute.
*Base.*—Rounded.
*Attachment.*—Base of the plant.
*Margin.*—Dentate.
*Texture of top surface.*—Glabrous to slightly tomentose.
*Texture of bottom surface.*—Glabrous.
*Appearance of top surface.*—Slightly glossy.
*Appearance bottom surface.*—Slightly glossy.
*Leaf internode length.*—Very close to form a basal rosette.
*Color.*—Young foliage upper side: RHS Yellow-Green 146A. Young foliage under side: RHS Yellow-Green 146A. Mature foliage upper side: Between RHS Yellow-Green 146A and 146B. Mature foliage under side: Between RHS Yellow-Green 146B and 146C.
*Venation.*—Type: Dichotomous; plunging into the limb at the upper surface; raised on the limb at the lower surface. Venation color upper side: RHS Yellow-Green 144B. Venation color under side: RHS Yellow-Green 144B.
*Petiole.*—Appearance: Long, tubular, rigid. Slightly flattened in older leaves. Length: Average range 13 to 17 cm. Diameter: Average range 0.3 to 0.4 cm. Pubescence: Glossy, slightly tomentose. Color: Between RHS Yellow-Green 144A and 144B.

Leaf at the nodes of the stems:

*Arrangement.*—Biternate.
*Average length.*—5 to 16 cm.
*Average width.*—4 to 13 cm.
*Overall shape of blade.*—Palmatipartite.
*Dissected leaves, describe lobes, quantity of dissection.*—Generally divided in 3 parts, each one of which is further divided in many deeply incised lobes.
*Apex.*—Acute.
*Base.*—Acute.
*Attachment.*—Petiolate.
*Margin.*—Entire to serrate near apex.
*Texture of top surface.*—Glabrous to slightly tomentose.
*Texture of bottom surface.*—Glabrous.
*Appearance of top surface.*—Glossy.
*Appearance bottom surface.*—Slightly glossy.
*Leaf internode length.*—Average 5 to 15 cm.
*Color.*—Foliage upper side: RHS Yellow-Green 146A. Foliage under side: RHS Yellow-Green 146C.
*Venation.*—Type: Dichotomous, plunging into the limb at the upper surface and raised on the limb at the lower surface. Venation color upper side: RHS Yellow-Green 144C. Venation color under side: RHS Yellow-Green 146C.
*Petiole.*—Appearance: Long, slightly flat, rigid. Length: Average 2 to 7 cm. Diameter: Average 0.2 to 0.5 cm. Pubescence: Glossy, slightly tomentose. Color: RHS Yellow-Green 144B.

FLOWER

Bloom period: Spring.
Vase life (cut flower): 12 to 14 days.
Flower longevity on plant: 5 to 7 days.
Persistent or self-cleaning: Self-Cleaning.
Bud:
*Closed bud*.—Shape: Broadly ovate with a sharp point. Length: 1.2 cm. Diameter: 1.0 cm. Color: RHS Yellow-Green 144C at apex; 144D at base.
*Slightly open bud*.—Shape: Broadly ovate. Length: 1.4 cm. Diameter: 1.5 cm. Color: Between RHS Yellow-Green 144B and 144C.
Flower size:
*Diameter*.—6 cm.
*Height*.—4 cm.
Corolla: Round, regular.
Petals:
*Arrangement*.—Semi-double; imbricated, disposed on the receptacle in very tight verticils. Size of petals variable, according to position, decreasing from exterior towards the center.
*Lobe length*.—2.7 cm.
*Lobe width*.—2.2 cm.
*Quantity*.—Numerous, more than 50.
*Texture*.—Silky, thin, glossy.
*Lobe apex*.—Rounded.
*Lobe shape*.—Obovate.
*Margin*.—Undulate.
*Aspect*.—Concave with moderately reflexed apex when fully open.
*Color when opening*.—Upper surface: RHS Greyed-Orange N163C; Yellow-Orange 17A at base. Lower surface: RHS Greyed-Orange N163B; Yellow 7B at base.
*Color fully opened*.—Upper surface: Between RHS Yellow-Orange 21A and 23A; Yellow 9A at base. Lower surface: RHS Orange 25B; Yellow-Orange 15A at base; flushed with Greyed-Orange169B from apex downwards.
Calyx/sepals:
*Quantity per flower*.—5 which fall before flower matures.
*Shape*.—Ovate.
*Length*.—1.4 cm.
*Width*.—0.6 cm.
*Apex*.—Acute.
*Base*.—Flat.
*Margin*.—Entire.
*Texture*.—Lower surface: Slightly tomentose. Upper surface: Slightly tomentose.
*Color*.—Upper Surface: RHS Yellow-Green 145C; Greyed-Orange 166C at edges and apex. Lower Surface: RHS Yellow-Green N144D; Greyed-Orange 166B at edges and apex.
Peduncle: None.
Pedicel:
*Length*.—Average 3 to 9 cm.
*Diameter*.—Average 0.2 to 0.3 cm.
*Color*.—Between RHS Yellow-Green 144A and 144B.
*Orientation*.—Upright.
*Pubescence*.—Slightly tomentose.
Fragrance: None.

REPRODUCTIVE ORGANS

Androecium:
*Stamens*.—Very numerous, short and completely surround the gynoecium.
*Anther shape*.—Slightly curved.
*Anther length*.—Average 0.5 cm.
*Anther color*.—RHS Yellow-Orange 15A; fading to 12A.
*Pollen*.—Sparse.
Gynoecium: The pistils are numerous, short, locked together at the center of the corolla, dome-shaped apocarpous gynoecium.
*Height*.—1.0 cm.
*Width*.—0.8 cm.
*Shape*.—Domed, ovate.
*Pistil color*.—RHS Yellow-Green N144C.

OTHER CHARACTERISTICS

Disease resistance: Typical for the species. Powdery mildew, leaf miner and rodent damage have all been observed in trials.
Drought tolerance and cold tolerance: More cold-hardy compared to other *Ranunculus* cultivars.
Fruit/seed production : Not observed.

What is claimed is:

1. A new and distinct cultivar of *Ranunculus* plant named 'ROCORANGE' as herein illustrated and described.

* * * * *